United States Patent [19]
Yavitz

[11] Patent Number: 5,649,922
[45] Date of Patent: Jul. 22, 1997

[54] APPARATUS AND METHOD FOR ALTERING CORNEAL TISSUE

[76] Inventor: Edward Q. Yavitz, 3828 Spring Creek Rd., Rockford, Ill. 61114

[21] Appl. No.: 503,101

[22] Filed: Jul. 17, 1995

[51] Int. Cl.⁶ .................................................. A61N 5/06
[52] U.S. Cl. .................................................. 606/4
[58] Field of Search .................. 606/4, 5, 6, 10, 606/11, 12, 17

[56] References Cited

U.S. PATENT DOCUMENTS

| | | | |
|---|---|---|---|
| 3,074,407 | 1/1963 | Moon et al. | |
| 4,156,124 | 5/1979 | Macken et al. | |
| 4,406,285 | 9/1983 | Villasenor et al. | |
| 4,461,294 | 7/1984 | Baron | |
| 4,840,175 | 6/1989 | Peyman | |
| 4,903,695 | 2/1990 | Warner et al. | 606/4 |
| 4,905,711 | 3/1990 | Bennett et al. | 606/4 |
| 5,092,863 | 3/1992 | Schanzlin | 606/5 |
| 5,108,412 | 4/1992 | Krumeich et al. | 606/4 |
| 5,437,657 | 8/1995 | Epstein | 606/4 |

FOREIGN PATENT DOCUMENTS

| | | | |
|---|---|---|---|
| 0531756 | 3/1993 | European Pat. Off. | 606/4 |
| 9201015 | 6/1992 | WIPO | 606/4 |
| 9401892 | 9/1994 | WIPO | 606/4 |

*Primary Examiner*—Lee S. Cohen
*Assistant Examiner*—Sonja Harris-Ogugua
*Attorney, Agent, or Firm*—Robert A. Van Someren

[57] ABSTRACT

An apparatus and method for treating vision disorders is disclosed. The apparatus and method incorporate a cutter which cuts into the corneal tissue of an eye. The corneal tissue proximate the lower region of the cut is then heated by, for instance, a laser which causes the tissue at that predetermined region to shrink. The shrinkage moves the cut plug with respect to the remainder of the eye to change the shape of the corneal surface and correct the problematic refractive error.

21 Claims, 2 Drawing Sheets

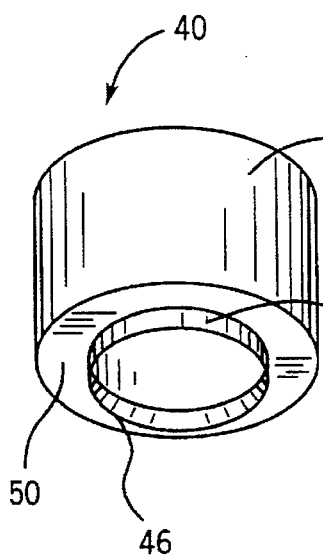
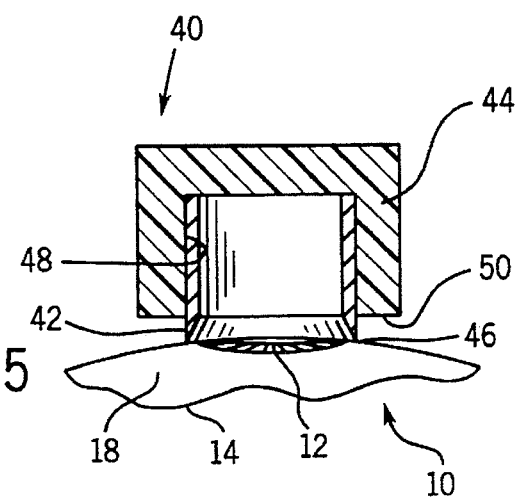
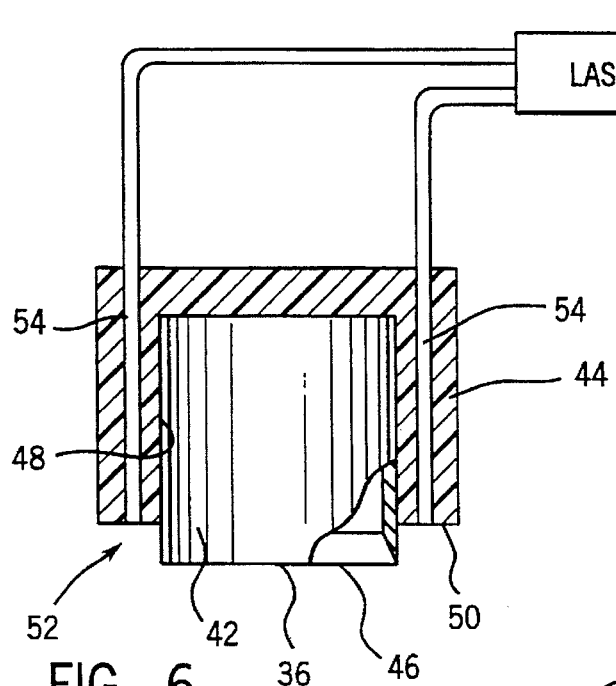
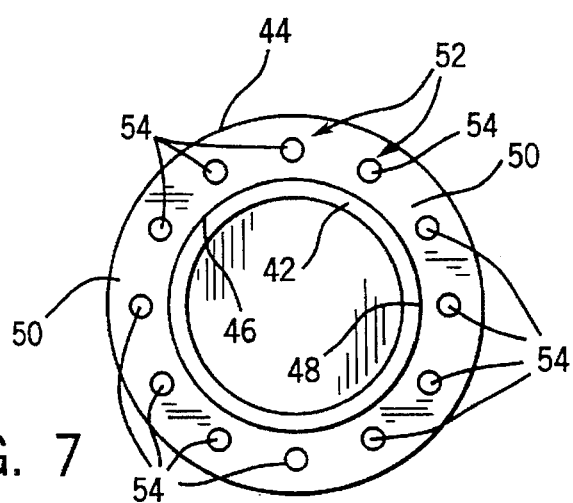

APPARATUS AND METHOD FOR ALTERING CORNEAL TISSUE

FIELD OF THE INVENTION

The present invention relates generally to a device and method for reshaping the cornea of an eye.

BACKGROUND OF THE INVENTION

Refractive errors such as nearsightedness and farsightedness can be reduced or corrected by reshaping the cornea of an eye. There are currently many methods for reshaping the cornea, including laser radial keratotomy and scalpel radial keratotomy. One problem with these procedures, particularly in correcting farsightedness, is the difficulty of gauging the effects of making incisions in the corneal surface.

One new technique involves heating the middle of the cornea in a radial pattern with a holmium laser. The heating causes the central cornea to bulge forward, thereby temporarily correcting for farsightedness. Unfortunately, the effect of the holmium laser alone is not permanent. Moreover, it is difficult to contain the laser to only those areas that are to be heated. It would be advantageous to have a device and a method for permanently reshaping the cornea that guarantees precision in setting the diameter, centration and depth of the incision.

SUMMARY OF THE INVENTION

The present invention features an apparatus for reshaping a defined area of corneal tissue about a pupil of an eye. The apparatus, according to one preferred embodiment of the invention, includes a cutter disposed to cut into the corneal tissue about the entire pupil to form a plug. A heating device is used to heat a region of corneal tissue proximate the plug which causes the plug to move with respect to its surrounding corneal tissue. The cutter may comprise a laser or a rigid blade while the heater may comprise a laser such as a holmium laser. Additionally, a guard may be attached to the cutter to precisely control cutting of a predetermined distance into the corneal tissue at each point of the cut.

According to another aspect of the invention, a method is featured for reshaping a predetermined area of corneal tissue surrounding a pupil of an eye. The eye is of the type having an epithelium layer, a Bowman's membrane layer, and a collagen stroma layer. The method includes the steps of providing a cutter adapted to cut or displace intrastromal relationships in the predetermined area of corneal tissue. The cutter is actuated to cut into the predetermined area of corneal tissue a desired distance, creating a plug of corneal tissue having a cut surface surrounding the pupil. A portion of the predetermined area of corneal tissue is then deformed proximate the cut surface until the plug is moved, either outwardly or inwardly depending on the necessary optical correction, a desired distance with respect to the surrounding corneal tissue.

BRIEF DESCRIPTION OF THE DRAWINGS

The invention will hereafter be described with reference to the accompanying drawings, wherein like reference numerals denote like elements, and:

FIG. 4 is a perspective representation of a cutting device according to a preferred embodiment of the invention;

FIG. 5 is a cross-sectional view of the device illustrated in FIG. 4 and disposed adjacent an eye;

FIG. 6 is a side view of another exemplary device used for cutting and altering corneal tissue; and FIG. 7 is a bottom view of the device illustrated in FIG. 6.

DETAILED DESCRIPTION OF THE PREFERRED EMBODIMENT

Figure 1:
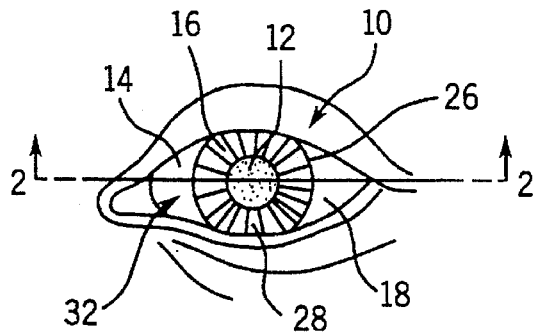
FIG. 1 is a front view of an eye that illustrates the cut portion of corneal tissue.

Referring generally to FIG. 1, an eye 10, such as a human eye, is disclosed. Eye 10 includes a pupil 12 surrounded by corneal tissue 14 and, for example, an iris 16. Corneal tissue 14 is bounded by a corneal surface 18.

Many vision disorders, such as nearsightedness and farsightedness, result from a slightly misshapen corneal surface 18. Theoretically, such disorders should be correctable by reshaping corneal surface 18 to compensate for the refractive errors causing the sight disorder. Practically, this may be accomplished according to the method and device described below.

Figure 2:
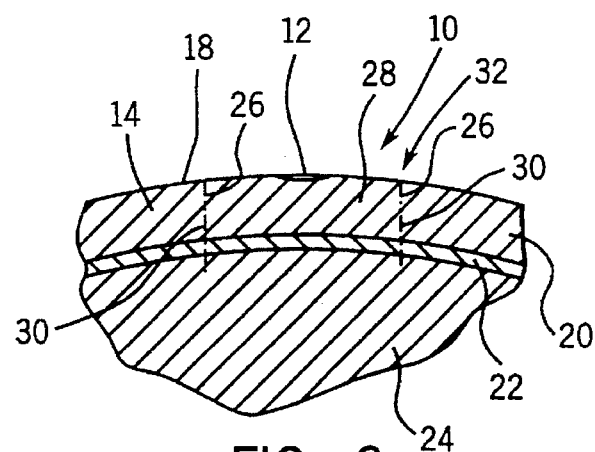
FIG. 2 is a cross-sectional view of FIG. 1 taken generally along lines 2—2 of FIG. 1.

As illustrated in FIG. 2, eye 10, particularly corneal tissue 14, includes a plurality of layers between corneal surface 18 and a more central region of the eye that includes, for instance, the lens of the eye (not shown). An outer or epithelium layer 20 is bounded by corneal surface 18. Inwardly from epithelium layer 20 is a membrane layer 22, known as Bowman's membrane layer. Inwardly from membrane layer 22 is a collagen layer 24 that extends towards the center of the eye.

According to the present inventive method, a cut 26 is made into eye 10 through corneal surface 18, and preferably through epithelium layer 20 and membrane layer 22. Cut 26 is illustrated in FIGS. 1 and 2 and preferably extends substantially about pupil 12. According to one embodiment of the invention, cut 26 may be circular and extend in a circular pattern about pupil 12 at a given distance from pupil 12. Thus, cut 26 generally forms a plug portion 28 defined by an outer cut surface 30.

Figure 3A:
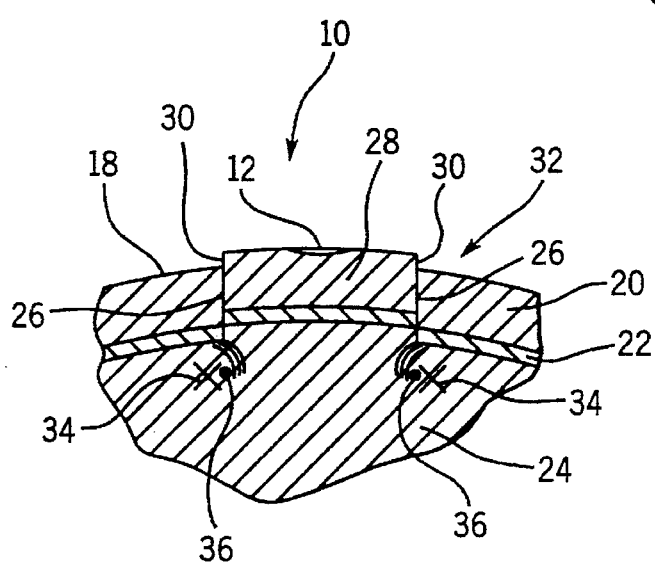
FIG. 3A is a cross-sectional view similar to that of FIG. 2 illustrating the corneal tissue after it has been treated.
Figure 3B:
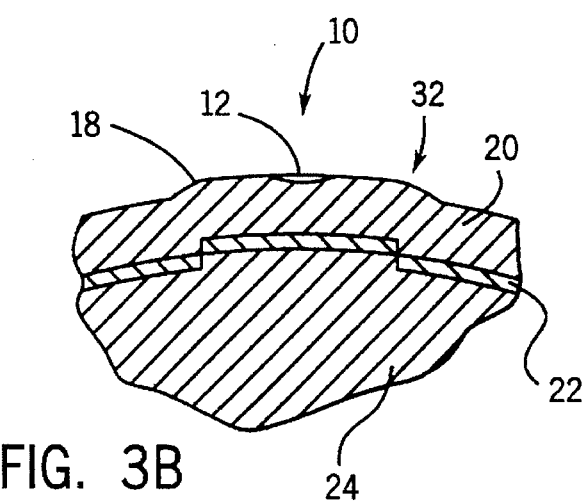
FIG. 3B is a cross-sectional view similar to that of FIG. 2 illustrating the corneal tissue after it has been treated and healed.

As illustrated in FIGS. 3A and 3B, a portion of the corneal tissue 14 may be deformed in a manner that moves plug portion 28 with respect to the remainder of the corneal tissue 14. Potentially, plug portion 28 can be moved inwardly with respect to eye 10 or outwardly with respect to the remainder of eye 10 as illustrated in FIG. 3A. Generally, plug portion 28 is moved slightly outwardly to correct refractive errors that lead to conditions such as hyperopia (farsightedness) or presbyopia.

As illustrated, plug portion 28 is cut from a predetermined region 32 of corneal tissue 14. By deforming a desired corneal portion 34, plug 28 is squeezed and moved slightly outwardly as illustrated in FIG. 3A. Cut 26 is then permitted to heal, thereby permanently affixing plug portion 28 in its new location with respect to the remainder of the corneal tissue 14, as illustrated in FIG. 3B.

To move plug portion 28 outwardly, it is preferred that corneal portion 34 be located proximate outer cut surface 30, preferably slightly outside and below outer cut surface 30 as indicated by each X in FIG. 3A. By shrinking this corneal portion 34 of corneal tissue 14, plug portion 28 is squeezed slightly outwardly to appropriately change the curvature of corneal surface 18. It should be noted that the necessary movement of plug portion 28 varies, depending on the type and severity of the vision disorder, but it is typically on the order of 20–80 microns. The movement illustrated in the Figures has been exaggerated merely for illustrative purposes. Also, corneal portion 34 may be within plug 28 if the desired motion of plug 28 is inward with respect to the surrounding corneal tissue. In either event, the displaced or separated intrastromal relationships recombine as the plug heals into place at its new location, thereby permanently changing the shape of the corneal surface.

The shrinking of corneal portion 34 and the consequent outward movement of plug portion 28 may be accomplished by selectively heating the corneal tissue at portion 34. Although the heating could be accomplished in a variety of ways, a laser of desired wavelength and intensity is preferably used. An example of one type of laser that has proved effective is a holmium laser. The laser energy causes corneal portion 34 of collagen layer 24 to shrink around plug portion 28 and force plug portion 28 outwardly. The effect of the laser may be enhanced by injecting a dye, such as the photodye Rose Bengal manufactured by Smith and Nephew of London, England, into the area of portion 34. Dye 36 may be injected either independently or at the time plug 28 is created by cut 26. In either event, the dye absorbs more of the laser energy creating a greater heating of region 34 with a lower energy laser. The lower energy laser tends to protect the surrounding corneal tissue.

Preferably, the laser light energy is split into multiple beams of light, e.g. eight, which are evenly spaced about plug 28 to cause uniform, simultaneous deformation of corneal tissue. It is also preferred that the heating be accomplished at the same time or shortly after plug 28 is cut to avoid swelling, hydration and detrimental changes to the cut corneal tissue.

Referring generally to FIG. 4, an apparatus 40 for reshaping predetermined region 32 of corneal tissue 14 is illustrated. Apparatus 40 includes a cutter 42 and a guard 44. Cutter 42 is preferably a blade, such as a trephine blade made from an appropriate metal, such as surgical steel. Cutter 42 is mounted to guard 44 and includes a cutting edge 46 (see FIGS. 4 & 5) designed preferably to cut substantially about the perimeter of pupil 12 at a given radius to create plug 28. In the most preferred embodiment, cutting edge 46 has a generally circular configuration.

Guard 44 preferably has a hollow interior 48 designed to receive cutter 42. The exact configuration can vary substantially without departing from the scope of the present invention, and cutter 42 may be fixedly mounted or adjustably mounted to permit retraction of cutting edge 46 into guard 44. However, during the cutting operation illustrated in FIG. 5, cutting edge 46 must be maintained at a predetermined distance from a leading edge 50 of guard 44. Leading edge 50 is designed to move into abutment with corneal surface 18 when cut 26 is formed by cutter 42. Thus, cutting edge 46 should remain fixed with respect to leading edge 50 during the cutting operation. In some applications, the distance between leading edge 50 and cutting edge 46 may vary at different points, but the predetermined distance at each point remains the same during the cutting operation.

Typically, cutting edge 46 extends at least 100 microns and up to 800 microns from leading edge 50. The exact distance is determined according to the type of vision disorder and the severity of that disorder. If a laser is used to cut the corneal tissue, the predetermined distance can precisely be controlled by controlling the intensity of the laser.

In the Figures, cutter 42 is exemplified by a circular trephine cutter, but a variety of cutters could be used. For example, certain lasers could potentially be used to provide cut 26 and create plug 28. An example is an excimer laser, such as those manufactured by the Laser Sight Company of Orlando, Fla. Movable blades could also be used to create cut 26 either fully or partially about the perimeter of pupil 12.

As illustrated in FIGS. 6 and 7, guard 44 may incorporate a light transmitting material 52 capable of transmitting laser light energy through guard 44 and towards corneal portion 34 of tissue 14. Light transmitting material 52 may be made of a variety of materials, such as quartz or optical fibers 54, as illustrated in FIGS. 6, and 7. Optical fibers 54 are oriented to direct laser light energy, supplied by a laser light source 56, to corneal portion 34 of tissue 14. An exemplary laser is a holmium laser, such as those manufactured by Sunrise Corp. of California or Summit Corp. of Massachusetts.

In the illustrated embodiment, the light transmitting material 52 extends through guard 44 and is uniformly disposed about leading edge 50 to provide a transfer of energy that heats corneal portion 34 in an evenly distributed manner about the circumference of plug 28. Thus, the heating of portion 34 is uniform, causing a uniform shrinking of the collagen layer proximate plug 28 to thereby precisely move plug 28 outwardly the desired amount.

Optionally, dye 36 may be coated on cutter 42 along cutting edge 46 to dye the corneal tissue disposed in proximity to plug 28 as cutter 42 is pressed into eye 10. As explained above, the dye 36 more readily absorbs the laser light energy to provide heating, and consequent shrinking, of the collagen layer proximate plug 28. This permits the use of a lower energy laser that is less likely to harm or effect tissues other than those proximate plug 28.

It will be understood that the foregoing description is of a preferred exemplary embodiment of this invention and that the invention is not limited to the specific forms shown. For example, the cutter may comprise a solid metal material, other solid materials, a laser or a variety of other cutting devices able to penetrate corneal tissue. The shape of any solid blade may be circular, oval, or otherwise shaped, depending on the desired type of plug to be moved with respect to the remainder of the eye. The deformation of the corneal tissue may be accomplished in a variety of ways including heating, chemical action, or other suitable procedures to cause the desired shrinkage or expansion of the tissue that adjusts the position of the plug. These and other modifications may be made in the design and arrangement of the elements without departing from the scope of the invention as expressed in the appended claims.

What is claimed is:

1. An apparatus for reshaping a defined area of corneal tissue about a pupil of an eye, the apparatus comprising:
    a cutter disposed to cut at least one predetermined distance into the corneal tissue at a location generally surrounding the pupil to form a plug of corneal tissue; and
    a heating device connected to the cutter and adapted to heat a region of corneal tissue proximate the plug.

2. The apparatus as recited in claim 1, wherein the heating device includes a laser.

3. The apparatus as recited in claim 2, wherein the heating device is connected to the cutter by the guard.

4. The apparatus as recited in claim 1, wherein the cutter includes a laser.

5. The apparatus as recited in claim 4, wherein the laser is an excimer laser.

6. The apparatus as recited in claim 1, wherein the cutter includes a cutting edge designed to cut the at least one predetermined distance uniformly along the entire length of the cut.

7. The apparatus as recited in claim 1, wherein the cutter includes a metal trephine which is mounted to a guard having a leading edge configured to rest against a corneal surface of the eye.

8. The apparatus as recited in claim 2, wherein a light transmitting material extends through the guard to direct laser energy to the region of corneal tissue.

9. The apparatus as recited in claim 8, wherein the light transmitting material comprises a fiber-optic material.

10. A method for reshaping a predetermined area of corneal tissue surrounding a pupil of an eye, the eye being of the type having an epithelium layer, a Bowman's membrane layer and a collagen stroma layer, the method comprising the steps of:

locating a cutter proximate the predetermined area of corneal tissue, the cutter being adapted to displace intrastromal relationships in the predetermined area of corneal tissue;

actuating the cutter to cut into the predetermined area of corneal tissue a desired distance to create a plug of corneal tissue having a cut surface surrounding the pupil; and deforming a portion of the predetermined area of corneal tissue proximate the cut surface until the plug is moved a desired distance with respect to the surrounding corneal tissue.

11. The method as recited in claim 10, wherein the step of deforming includes the step of heating the portion of the predetermined area of corneal tissue.

12. The method as recited in claim 11, wherein the step of heating includes the step of directing a laser to the portion of the predetermined area of corneal tissue.

13. The method as recited in claim 12, further comprising the step of supplying a dye to the portion of the predetermined area of corneal tissue.

14. The method as recited in claim 10, wherein the step of locating a cutter includes locating a cutter blade having a cutting edge proximate the predetermined area.

15. The method as recited in claim 14, wherein the step of locating a cutter includes locating a cutter blade having a metal trephine blade proximate the predetermined area.

16. The method as recited in claim 14, further comprising the step of mounting the cutter blade within a guard having a leading edge configured to rest against a corneal surface of the eye.

17. The method as recited in claim 16, wherein the step of mounting includes providing a cutting position in which the cutting edge extends at least 100 microns from the leading edge.

18. The method as recited in claim 17, further comprising the steps of:

orienting a light transmitting material to direct a laser to the portion of the predetermined area of corneal tissue; and directing the laser through the light transmitting material.

19. The method as recited in claim 18, wherein the step of directing includes directing the laser through optical fibers.

20. The method as recited in claim 16, further comprising the step of at least partially coating the cutter blade with a dye.

21. The method as recited in claim 10, wherein the step of actuating includes the step of cutting through the Bowman's membrane layer.

* * * * *